United States Patent [19]

Hem et al.

[11] 4,242,328

[45] * Dec. 30, 1980

[54] PROCESS AND COMPOSITIONS

[75] Inventors: Stanley L. Hem, West Lafayette; Joe L. White, Lafayette, both of Ind.

[73] Assignee: Purdue Research Foundation, West Lafayette, Ind.

[*] Notice: The portion of the term of this patent subsequent to Oct. 7, 1992, has been disclaimed.

[21] Appl. No.: 72,206

[22] Filed: Sep. 4, 1979

Related U.S. Application Data

[63] Continuation of Ser. No. 845,198, Oct. 25, 1977, abandoned, which is a continuation-in-part of Ser. No. 566,254, Apr. 9, 1975, Pat. No. 4,059,681, which is a continuation-in-part of Ser. No. 360,043, May 14, 1973, abandoned.

[51] Int. Cl.$^3$ ............... C01B 31/24; A01N 11/00; A61K 33/10; C01F 7/02

[52] U.S. Cl. ............... 424/157; 424/156; 423/419 P; 423/427; 423/630

[58] Field of Search ............ 423/419 P, 420–422, 423/428, 430, 625, 628, 629; 424/156–158, 154

[56] References Cited

U.S. PATENT DOCUMENTS

| | | | |
|---|---|---|---|
| 2,783,179 | 2/1957 | Grote | 423/419 P |
| 3,698,861 | 10/1972 | Pascoe et al. | 423/629 |
| 3,911,090 | 10/1975 | Hem et al. | 423/419 P |
| 4,053,568 | 10/1977 | Madaus et al. | 423/419 P |
| 4,059,681 | 11/1977 | Hem et al. | 423/419 P |

OTHER PUBLICATIONS

Kerkhof et al., pH Stat Titration of Aluminium Hydroxide Gel, Journal of Pharmaceutical Sciences, vol. 66, #11, Nov. 77, p. 1528–1532.

Serna et al., Structural Survey of Carbonate Containing Antacids, Journal of Pharmaceutical Sciences, vol. 67, #3, Mar. 78, pp. 324–327.

Schwartz et al., Intragranular Starch: Comparison of Starch USP And Modified Cornstarch, J. of Pharmaceutical Sciences, vol. 64, #2, Feb. 75, pp. 328–332.

Staley Manufacturing Co. Technical Data, TDS #200, 960211 STA—Rx® 1500 Starch, undated.

*Primary Examiner*—O. R. Vertiz
*Assistant Examiner*—Gary P. Straub
*Attorney, Agent, or Firm*—John R. Nesbitt; Robert E. Harris

[57] ABSTRACT

Dried amorphous aluminum hydroxide gels having substantial acid reacting capability over an extended period of time are prepared by drying the gel after contacting the aqueous liquid gel with an inert organic solvent of sufficient solubility in water to replace water in the gel. The dried gel product and pharmaceutical compositions comprising the gel are also novel.

8 Claims, No Drawings

PROCESS AND COMPOSITIONS

CROSS REFERENCE TO RELATED APPLICATIONS

This application is a continuation of U.S. Application Ser. No. 845,198 filed Oct. 25, 1977, now abandoned which is a continuation-in-part of U.S. Application Ser. No. 566,254 filed Apr. 9, 1975 and now U.S. Pat. No. 4,059,681 issued Nov. 22, 1977, which is a continuation-in-part of U.S. Application Ser. No. 360,043 filed May 14, 1973, now abandoned.

BACKGROUND OF THE INVENTION

Aluminum hydroxide gel is a widely used antacid. It possesses many of the properties of an ideal antacid such as acid consuming capacity and non-absorbability. Many effective antacid fluid dosage forms currently marketed utilize aluminum hydroxide gel. However, when aqueous aluminum hydroxide gel is used to produce a dried gel which can be formulated into solid dosage forms, its total antacid reactivity, as well as acid reaction rate, is decreased. Of even greater potential significance, the aging of dried aluminum hydroxide gel at ambient or elevated temperature results in significant losses in antacid reactivity. An antacid preparation which is initially active can become inactive over a relatively short period of time. However, the convenience of a solid antacid dosage form over a fluid dosage form is readily appreciated and makes highly desirable the development of an initially acid reactive dried aluminum hydroxide gel which maintains its acid reactivity for an extended period of time.

SUMMARY OF THE INVENTION

In accordance with this invention there is a process for preparing a dried amorphous antacid aluminum hydroxide gel which comprises contacting an amorphous aqueous aluminum hydroxide gel with an inert organic solvent of sufficient solubility in water to replace water in the gel; removing the inert organic solvent; drying the amorphous aluminum hydroxide gel to an acid reactant stable amorphous powder having substantial acid reacting capability over an extended period of time.

A further aspect of the invention is a composition which comprises a dried aluminum hydroxide gel with a surface area minimum of 150 m$^2$/gm. and a pH stat $t_{50}$ value of from about six to about 20 minutes.

A still further aspect of the invention is a pharmaceutical composition which comprises in association with a solid pharmaceutical carrier, a dried amorphous aluminum hydroxide gel, said gel having a minimum surface area of 150 m$^2$/gm. and a pH stat $t_{50}$ value of about six to about 20 minutes.

DETAILED DESCRIPTION OF THE INVENTION

The aqueous amorphous aluminum hydroxide gel which is dried is a standard acid reactive aqueous gel which can be obtained from various manufacturers such as Chattem Chemical Company, Reheis, Barcroft, and J. T. Baker. An amorphous aqueous aluminum hydroxide gel which meets the United States Pharmacopeia 19th Revision specification is preferably employed. If it is desirable to initially prepare an aqueous amorphous aluminum hydroxide gel rather than purchasing a commercially prepared gel, art-known methods for preparing an acid reactive gel can be employed. For example, antacid active amorphous aqueous gels are prepared through the reaction of a water soluble aluminum salt such as aluminum chloride, aluminum sulfate or the like, and a basic aqueous solution such as an alkali metal carbonate or bicarbonate solution. Although the reason is not clearly understood, gels of higher antacid activity are prepared from carbonate or bicarbonate-containing bases.

Once the aqueous gel is obtained, it is contacted with an inert organic solvent of sufficient water solubility to replace water in the gel. The term inert as used herein refers to the lack of reactivity of the organic solvent with the gel. Examples of organic solvents which can be employed in this invention are those solvents which are miscible with water, for example, methanol, ethanol, propanol, isopropol, acetone, acetaldehyde, dimethylformamide, formamide, tetrahydrofuran, 1,3-dioxane, 1,4-dioxane, pyridine and other organic solvents miscible in water. Inert organic solvents which are not miscible in water but which can be employed are higher alcohols such as butanols and pentanols, esters such as ethyl acetate, and higher homologues thereof having one to three carbon atoms attached to the acyl moiety; ketones having four to six carbon atoms, inclusive, and the like. For convenience and ease of handling the gel, the inert organic solvent should be added to the aqueous gel in such quantities that a single liquid phase is present. By definition, a water miscible solvent will only form a single phase with water. For practical reasons, the single phase should exist for other organic solvents not miscible in water when the solvent is added in quantities up to a 1:1 ratio with respect to the volume of aqueous gel. It should be noted that organic solvents may be used in mixtures for replacement of the water in the gel. For example, a 1:1 ratio, methanol (50%), benzene (50%): aqueous gel volume, still maintains a single phase with the aqueous gel even though benzene, added alone to the aqueous gel, would create two phases.

The organic solvent may be added to the gel in various proportions and the addition of solvent repeated after removal as well. For preparing a dried gel with high acid reactivity as measured by the pH stat $t_{50}$ value, as well as the Rossett-Rice test, ethanol should be added to the aqueous gel at a volume of 3:1. The water and ethanol are removed by decantation, vacuum filtration, or preferably centrifugation, and the entire treatment step should be repeated twice. As a balance between cost, handling and acid reactivity, ethanol should be added to the gel at a volume ratio of 2:1, water and ethanol removed and then followed by a 1:1 addition of ethanol. The secondary treatment volumes of organic solvent are measured on the basis of the original gel volume.

At each treatment step, the aluminum hydroxide gel is maintained as a moist cake. Following the final solvent treatment, the gel is dried using standard means such as spray drying, vacuum drying, forced air drying, drum drying, and the like.

The dried amorphous aluminum hydroxide gel prepared by this process has high antacid reactivity as measured by the Rossett-Rice time and the pH stat $t_{50}$ time. Rossett-Rice time is the length of time a quantity of the dried gel equivalent to 300 mgs. of aluminum oxide dispersed in 70 milliliters of 0.1 N hydrochloric acid and 30 milliliters of water at 37° C. remains at a pH between 3 to 5 as 0.1 N hydrochloric acid is added to the mixture at a rate of 4 milliliters per minute. The pH stat test is a more sensitive test of acid reactivity. This test measures the volume of acid required to maintain pH at a preset value as a function of time. The $t_{50}$ is the time required for one-half of the antacid to be consumed. The rate of loss of antacid activity as measured by Rossett-Rice time of gels prepared after drying from water is substantially greater than for gels prepared after drying from an inert organic solvent. The rate constant for loss of reactivity for gels dried from watrer is about 0.48/month at 40° C. in contrast to about 0.071/month at 40° C. for gels dried from the organic solvent. This is a significant difference which is reflected in a much greater retention of acid reactivity at room temperature by the gels of the invention. This difference illustrates the stability of the product prepared by this process over an extended period of time. The term "extended period of time" as used in this specification and claims, indicates a period of time over which the dried gel is capable of neutralizing acid at such a rate and at such a pH that a pharmaceutical composition comprising that gel would have a useful shelf life. A period of at least two years is contemplated. It is this extended antacid activity which distinguishes the amorphous gel prepared by the process of this invention from the gels of the art dried from water and allows the preparation of a potent antacid for therapeutic purposes.

This extended antacid activity is manifested by the composition characteristics of an increased surface area over gels prepared by drying from water in combination with certain pH stat $t_{50}$ values. A minimum surface area of 150 m$^2$/gm. of aluminum hydroxide gel as measured by nitrogen adsorption appears to be necessary. A minimum surface area above 170 m$^2$/gm. is preferred. The composition has a pH stat $t_{50}$ time of about six to about 20 minutes. A pH stat $t_{50}$ of about six to about 15 minutes is preferred. The aluminum oxide content of the gel, as measured by the United States Pharmacopeia 18th Revision assay system can vary significantly and still provide gels which are antacid active for an extended period of time. For example, aluminum oxide weight percentages can vary from about 40 to about 63% and still maintain antacid active gels. A preferred range of aluminum oxide is 45 to 59%. The 18th Revision of the United States Pharmacopeia discloses a range of 50-57.5%. Dried gels within this range are active and stable. The percentage aluminum oxide is dependent upon the drying time and does not appear to be intrinsically associated with extended antacid activity. However, amorphous gels dried from water seem to be required to fall within the 50-57.5% range of the U.S.P. to be active for even a short period of time.

The dried amorphous aluminum hydroxide gel of this specification is compounded into oral solid dosage pharmaceutical compositions for administration to individuals requiring antacid therapy. These oral, solid dosage forms are chewable or swallowable, the latter being preferred because of the chalky nature of the conventional chewable dosage form. The swallowable dosage form can be either a tablet or a capsule. When formulated into tablet form, the usual excipients can be employed, however, a strong disintegrant such as starch (for example, STA-Rx$^R$) is preferred for appropriate antacid action.

Following is an example in accordance with the invention. This example is intended to illustrate the invention concepts but not limit them.

EXAMPLE 1

In a 5 liter beaker, an 11.4% aqueous solution containing 0.755 moles of aluminum chloride hexahydrate is added to an aqueous solution containing 2.8% sodium carbonate (0.57 moles) and 4.5% sodium bicarbonate (1.336 moles). The mixture is stirred for a few minutes at room temperature; and the aluminum hydroxide gel formed is washed several times with de-ionized water to remove the residual salts.

The gel is then treated three times with a volume of ethanol equal to the volume of aluminum hydroxide gel (about 500 ml.) by thoroughly dispersing the gel in the alcohol and filtering through a Buchner funnel using 1 filter paper, being careful to maintain the aluminum hydroxide as a moist cake. The final product is dried at an elevated temperature.

The Rossett-Rice time, lag time, acid consuming capacity, and pH stat $t_{50}$ on aging of the above dried amorphous aluminum hydroxide gel indicate a substantially more potent product than similarly prepared gels dried from water. The Rossett-Rice time and pH stat $t_{50}$ tests were previously defined. The lag time is the length of time required for the pH to reach 3.0 after starting the addition of the hydrochloric acid in the Rossett-Rice time determination. Acid consuming capacity is the method used in U.S.P. 19th Revision.

The pH stat $t_{50}$ values in this specification are obtained under the following conditions. A sample of dried aluminum hydroxide gel containing 38 mg. of aluminum hydroxide, as measured by the assay procedure of the United States Pharmacopeia, 19th Revision, is dispersed in 22 ml. of distilled water in a 50 ml. beaker. The pH stat $t_{50}$ value for a pH of 3.0 is then obtained for this sample using a typical pH stat titrator assembly with a stirrer operating at 900 rpm. The particular pH stat titrator assembly is not unduly significant. Such assemblies are available from Mettler. Beckman and Radiometer A/S (Copenhagen, Denmark). The specific assembly components used were obtained from Radiometer and are:

pH meter PHM 26
Titrator TTT II
Autoburet ABU12 (2.5 ml.)
Titration Assembly TTA3
Recorder SBR 2

I claim:

1. A process for preparing a dried amorphous therapeutic antacid aluminum hydroxide gel which comprises contacting an amorphous aqueous aluminum hydroxide gel with an inert organic solvent, of sufficient solubility in water to maintain a single phase when contacted in a 1:1 volume ratio with the aqueous gel, to replace water in the gel, removing the inert organic solvent; drying the amorphous aluminum hydroxide gel to an acid reactant stable amorphous powder that is no less than about 40 weight percent aluminum oxide with said powder having an initial pH-stat $t_{50}$ value with a range of about 6 to 20 minutes and retaining a pH-stat $t_{50}$ time within said range for a period of at least 24 months beyond the date of drying.

2. A process in accordance with claim 1 wherein the organic solvent is methanol, ethanol, propanol, isopropanol, acetone, acetaldehyde, dimethylformamide, formamide, tetrahydrofuran, 1,3-dioxane, 1,4-dioxane or pyridine.

3. A process in accordance with claim 2 wherein the solvent is methanol, ethanol, propanol, isopropanol or acetone.

4. A process in accordance with claim 3 wherein the solvent is methanol or ethanol.

5. A process in accordance with claim 1 wherein the organic solvent is a mixture of organic entities.

6. A process in accordance with claim 1 wherein the powder is from about 40 to about 63 weight percent aluminum oxide.

7. A process in accordance with claim 6 wherein the powder is from about 45 to about 59 weight percent aluminum oxide.

8. A process for preparing a dried amorphous therapeutic aluminum hydroxide gel which comprises contacting an amorphous aqueous aluminum hydroxide gel with an inert organic solvent of sufficient water solubility to replace water in the gel; removing the inert organic solvent; drying the amorphous aluminum hydroxide gel to an acid reactant stable amorphous powder having a Rossett-Rice reactivity rate constant loss of less than about 0.1/month at 40° C. to thereby provide substantial acid reacting capability over an extended period of time beyond the date of drying.

* * * * *